United States Patent [19]

Arndt et al.

[11] 4,073,793
[45] Feb. 14, 1978

[54] 5-ALKYLUREIDO-1,3,4-THIADIAZOL-2-YL-SULFONYL-ACETIC ACID DERIVATIVES

[75] Inventors: Friedrich Arndt; Ludwig Nüsslein, both of Berlin, Germany

[73] Assignee: Schering Aktiengesellschaft, Berlin and Bergkamen, Germany

[21] Appl. No.: 759,558

[22] Filed: Jan. 14, 1977

[30] Foreign Application Priority Data

Jan. 16, 1976   Germany ............................. 2601988

[51] Int. Cl.² ...................... A01N 9/12; C07D 285/12
[52] U.S. Cl. .................................. 260/306.8 D; 71/90
[58] Field of Search ................................. 260/306.8 D

[56] References Cited

U.S. PATENT DOCUMENTS 3,773,780   11/1973   Metzger et al. ............. 260/306.8 D

FOREIGN PATENT DOCUMENTS 743,614   6/1970   Belgium ........................ 260/306.8 D Primary Examiner—R. J. Gallagher
Attorney, Agent, or Firm—Michael J. Striker

[57] ABSTRACT

(5-Alkylureido-1,3,4-thiadiazol-2-ylsulfonyl) acetic acid derivative of the formula

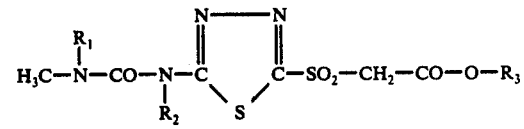

in which $R_1$ and $R_2$ are hydrogen or alkyl and $R_3$ is hydrogen, alkyl, univalent metal equivalent, an ammonium group or an alkyl ammonium group. The compositions are used for herbicidal purposes as the active agent in herbicide compositions.

5 Claims, No Drawings

5-ALKYLUREIDO-1,3,4-THIADIAZOL-2-YL-SULFONYL-ACETIC ACID DERIVATIVES

BACKGROUND OF THE INVENTION

The invention relates to 5-alkylureido-1,3,4-thiadiazol-2-yl-sulfonyl acetic acid derivatives.

(5-alkylureido-1,3,4-thiadiazol-2-ylthio)-carboxylic acids and their derivatives have already been proposed in a general way as herbicidal compositions in West German Pat. No. 1,817,949 without, however, naming acetic derivatives. Tests have shown that thioacetic acid derivatives of this class of compounds do not possess any herbicidal properties.

SUMMARY OF THE INVENTION

It has now been found that compounds of the general formula

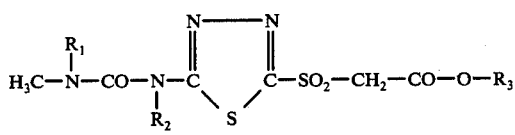

(I)

in which $R_1$ and $R_2$ are hydrogen or alkyl and $R_3$ is hydrogen, alkyl, a univalent metal equivalent, an ammonium group or an alkyl ammonium group, have an action regarding plant growth and can be used as defoliants, desiccants, herbicides and particularly weed killers.

Among these derivatives superior herbicidal action have those in which in the above formula $R_1$ and $R_2$ are hydrogen or methyl, $R_3$ is hydrogen, alkyl of 1 to 4 carbon atoms, a univalent metal equivalent, an ammonium group or an alkyl ammonium group.

The alkyl radicals may for instance be methyl, ethyl, propyl, isopropyl, butyl, sec.-butyl, isobutyl and tert.-butyl and as alkylammonium groups triethylammonium, tris-(2-hydroxy-(ethyl)-ammonium, tetramethylammonium and tetrabutylammonium.

Among the univalent metal equivalents there are Na, K, Ca/2, Mg/2, $NH_4$ and others.

It should be understood in this connection that compounds in which R is a metal equivalent, an ammonium or an alkyl ammonium group are present predominantly in ionized form.

The compounds of the invention can for instance be used as overall herbicides to destroy wasteland and shrubbery or they can be used as selective herbicides for agricultural crops.

They are particularly useful against monocotyloid weeds, such as Poa, *Eleusine indica,* Setaria, Echinochloa, Digitaria, *Avena fatua,* Alopecurus and Sorghum halepense and dicotyloids, such as, Stellaria, Senecio, Matricaria, Lamium, Centaurea, Amaranthus, Galium, Chrysanthemum, Ipomea, Polygonum and Xanthium.

As agricultural crops in which the compounds are useful may be mentioned, for instance, barley, oats, wheat, rice, maize, peanuts, peas, potatoes and others. Apart from their broad spectrum of action and high selectivity, their effectiveness against harmful grasses, in particular millet grasses, is noteworthy since any activity against these grasses by the present status of the art has been very difficult to induce. The compounds of the invention in this respect are superior in their activity as compared with prior art compounds which have a similarly directed activity.

Against seed weeds the amount usually used is relatively small and is between about 0.3 and 1.5 kg of active agent per about 2.5 acres.

The compounds of the invention can either be used individually or in mixtures with each other or in mixture with other agents. Depending on the particular purpose of the application they may be used together with defoliants, plant protecting agents and pesticides.

An increased action and speed of action can be obtained for instance by activity increasing additives such as organic solvents, crosslinking agents and oils. This in turn may result in a reduction of the amount of active agent proper.

The compounds of the inventions and their mixtures are preferably used in the form of compositions such as powders, dusting agents, granulates, solutions, emulsions or suspensions. There may be used liquid and/or solid carrier materials or diluents and, if desired, crosslinking, adhesion, emulsion and/or dispersion aids.

Suitable liquid carriers are for instance water, aliphatic and aromatic hydrocarbons, such as benzene, toluene, xylene, cyclohexanone, isophorone, dimethylsulfoxide, dimethylformamide, and furthermore mineral oil fractions.

As solid carrier materials there may be used minerals and earths, for instance tonsil, silica gel, talc, kaolin, attapulgite clay, limestone, silicic acid and plant products, such as flours.

There may be added surface active agents such as calciumlignosulfonate, polyoxyethylene alkylphenyl ether, naphthaline sulfone acids and their salts, phenolsulfone acids and their salts, formaldehyde condensates, fatty alcoholsulfates as well as substituted benzosulfone acids and their salts. The amount of active agent in the various compositions can be varied widely. The compositions may for instance contain about 10 to 80% by weight of active agent, about 90 to 20% by weight of liquid or solid carrier material and, if desired, up to 20% by weight of surface active agent.

The application of the compositions can be effected in conventional form. For instance, if water is used as the carrier material there may be a total spray mass of about 100 to 1000 liter per about 2.5 acres. The compositions can be used both in the so-called "low volume" and "ultra low volume" procedure as well as in the form of so-called microgranulates.

If it is desired to broaden the spectrum of activity or to destroy the entire flora of a wasteland, it may be useful to add still other herbicides.

PROCESS OF MAKING

The compounds of the inventions may be made in various ways.

[A] Compounds of the general formula

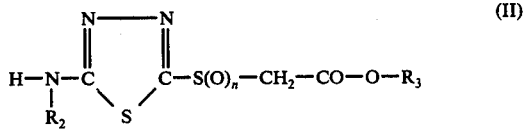

(II)

may be reacted with
(a) carbamoylchlorides of the formula

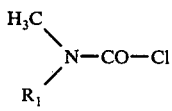

(b) phosgene and amines of the formulae

COCl$_2$ and

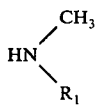

(c) carbamic acid esters of the formula

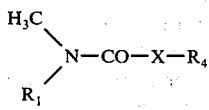

or (d) if R$_1$ in the final product is to be H with methylisocyanate (CH$_3$—NCO).

[B] Carbaminic(acid)ester of the formula

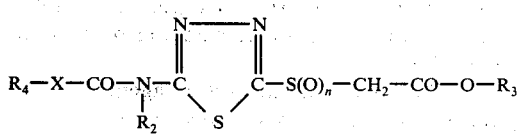 (III)

may be reacted with an alkylamine of the formula

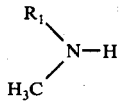

The reaction can be carried out in the presence of an inert solvent and in the presence of an acid acceptor. The product of the reaction may be treated then with an oxidizing agent in order to obtain the compounds of the invention.

In all of the above formulae, R$_1$ and R$_2$ are hydrogen or alkyl, R$_3$ is hydrogen, alkyl, a univalent metal equivalent, an ammonium group or an alkylammonium group, R$_4$ is alkyl or phenyl, X is oxygen or sulfur and $n$ is 0 or 2.

The starting products for making the compounds of the invention are known or can be made by conventional processes.

Where hydrochloric acid is produced in the process acid, acceptors are added, such as, tertiary amines, for instance, triethylamine or N,N-dimethylaniline, pyridine bases, or suitable inorganic bases such as oxides, hydroxides and carbonates of alkali metals or earth alkali metals.

The reaction is carried out between a temperature of −20° and +100° C, preferably at room temperature.

The components of the reaction are used in about equimolar amounts. Suitable reactants are solvents which are inert as to the components. As such may be mentioned aliphatic and aromatic hydrocarbons, such as petroleum ether, cyclohexane, benzene, toluene, and xylene, halogenated hydrocarbons, such as methylene chloride, chloroform, carbon tetrachloride and halogenated ethylenes, ether-type compounds like diethyl ether, diisopropyl ether, tetrahydrofuran and dioxane, ketones like acetone, methylisobutylketone and isophorone, esters, like acetic acid and ethylester, acid amides, like dimethylformamide and hexamethylphosphoric acid triamide, carboxylic acid nitriles, such as acetonitrile and many others.

As oxidizing agents there may be used inorganic or organic agents. As inorganic oxidizing agents there are for instance useful chlorine or potassium permangamate or chromic acid and their salts or nitric acid or hydrogen peroxide.

As organic oxidizing agents there may be used hydroperoxides such as tert. butylperoxide, or acids like m-chloroperbenzoic acid, etc. or N-halogeno acid amides like N-bromosuccinimide or others.

For one mol of thio compound there are preferably used four equivalents of oxidizing agents or an excess thereof in the temperature range between 0° and 100° C.

As reaction media there may be used organic solvents such as carboxylic acids, for instance formic acid and acetic acid, and ethers like dioxane, ketones, e.g. acetone, acid amides e.g. dimethylformamide, nitriles, like acetonitrile or others. These acids may be used by themselves or in mixture with water.

The free (5-methylureido-1,3,4-thiadiazol-2-yl-sulfonyl)-acetic acids are preferably obtained by hydrolysis of the esters in an alkyline environment and subsequent addition of mineral oil acids. The usual neutralization with organic or inorganic bases results in the corresponding salts.

EXAMPLES

The following Examples will further illustrate the making of the compounds of the invention.

EXAMPLE A

[5-(1,3,3-trimethylureido-1,3,4-thiadiazol-2-ylsulfonyl]-acetic acid tert. butylester 36.5 g of [5-(1,3,3-trimethylureido)-1,3,4-thiadiazol-2-ylthio]-acetic acid tert. butylester of a b.p. of 76° to 78° C are dissolved in 130 ml of glacial acetic acid and 20 ml water. Potassium permanganate is then added to this solution in batches and in a total amount of 20.55 g at a temperature of 40° C. The solution is then stirred for an additional 30 minutes and the manganese dioxide which precipitates in the mixture after cooling to 0° C is then reduced by dropwise addition of a solution of 20.9 sodium metabisulfite in 100 ml water. The separated oil is taken up in methylene chloride, the organic phase is washed twice with water, dried with magnesium sulfate and concentrated to dryness in a vacuum. There remain 34.4 g (85.9% of the theoretical value) of [5-(1,3,3-trimethylureido-1,3,4-thiadiazol-2-ylsulfonyl]-acetic acid tert. butylester; m.p. 130° to 132° C. The compound melts after recrystallizing from ethanol at 144° C.

EXAMPLE B

[5-(1,3-dimethylureido)-1,3,4-thiadiazol-2-ylsulfonyl]-acetic acid 15.4 g of [5-(1,3-dimethylureido)-1,3,4-thiadiazol-2-ylsulfonyl]-acetic acid methyl ester were suspended in a solution of 2 g of sodium hydroxide in 100 ml water and were stirred at room temperature for 30 minutes which caused the dissolving of the compound. After acidifying with concentrated hydrochloric acid the precipitated compound was removed by suction, washed with water and dried in a vacuum. There were thus obtained 14.6 g (99% of the theoretical value) of [5-(1,3-dimethylureido)-1,3,4-thiadiazol-2-ylsulfonyl]-acetic acid methyl ester; m.p. 151° C (decomposed).

EXAMPLE C

Triethylammonium salt of [5-(1,3-dimethylureido)-1,3,4-thiadiazol-2-ylsulfonyl]-acetic acid 2.7 ml of triethylamine were added dropwise while stirring to a suspension of 5.6 g of [5-(1,3-dimethylureido)-1,3,4-thiadiazol-2-ylsulfonyl] acetic acid in 6 ml water. During the addition a highly viscous mass was formed which therefore had to be diluted with a small amount of methanol. The reaction mixture was then stirred for another hour, washed and dried in a vacuum. The yield was 4.55 g (60.5% of the theoretical value) of [5-(1,3-dimethylureido)-1,3,4-thiadiazol-2-ylsulfonyl]-acetic acid triethylammonium salt; m.p. 177° C (decomposed).

EXAMPLE D

[5-(1,3-dimethylureido)-1,3,4-thiadiazol-2-ylsulfonyl]-acetic acid methyl ester

A solution of 2.50 g of (5-methylamino-1,3,4-thiadiazol-2-yl-sulfonyl) acetic acid methyl ester, (m.p. 118° C) in 30 ml tetrahydrofuran was reacted while stirring with 0.9 ml methylisocyanate and was kept overnight at 30° C. The solvent was then distilled off in a vacuum and the remaining residue was recrystallized from ethanol. There were thus obtained 1.10 g (35.9% of the theoretical value) of [5-(1,3-dimethylureido)-1,3,4-thiadiazol-2-ylsulfonyl]-acetic acid methylester; m.p. 157° C.

In an analogous manner the following acetic acid derivatives of the invention were produced.

| Compounds | Physical constants |
| --- | --- |
| [5-(1,3-dimethylureido)-1,3,4-thiadiazol-2-ylsulfonyl]-acetic acid | m.p. 151° C decomposed |
| [5-(1,3-dimethylureido)-1,3,4-thiadiazol-2-ylsulfonyl]-acetic acid triethylammonium salt | m.p. 177° C decomposed |
| [5-(1,3-dimethylureido)-1,3,4-thiadiazol-2-ylsulfonyl]-acetic acid methylester | m.p. 157° C |
| [5-(3-methylureido)-1,3,4-thiadiazol-2-ylsulfonyl]-acetic acid methylester | m.p. 184° C |
| [5-(3-methylureido)-1,3,4-thiadiazol-2-ylsulfonyl]-acetic acid | decomposed |
| [5-(1,3-dimethylureido)-1,3,4-thiadiazol-2-ylsulfonyl]-acetic acid ethylester | m.p. 136° C |
| [5-(1,3,3-trimethylureido)-1,3,4-thiadiazol-2-ylsulfonyl]-acetic acid methylester | m.p. 96° C |
| [5-(1,3,3-trimethylureido)-1,3,4-thiadiazol-2-ylsulfonyl]-acetic acid | m.p. 133° C decomposed |
| [5-(1,3-dimethylureido)-1,3,4-thiadiazol-2-ylsulfonyl]-acetic acid potassium salt | m.p. 145° C decomposed |
| [5-(1,3-dimethylureido)-1,3,4-thiadiazol-2-ylsulfonyl]-acetic acid sodium salt | m.p. 147° C decomposed |
| [5-(1,3,3-trimethylureido)-1,3,4-thiadiazol-2-ylsulfonyl-acetic acid ethylester | m.p. 56° C |
| [5-(1,3-dimethylureido)-1,3,4-thiadiazol-2-ylsulfonyl-acetic acid tert. butylester | m.p. 112° C |
| [5-(1,3,3-trimethylureido)-1,3,4-thiadiazol-2-ylsulfonyl]-acetic acid potassium salt | m.p. 110° C |
| [5-(1,3,3-trimethylureido)-1,3,4-thiadiazol-2-ylsulfonyl]-acetic acid ammonium salt | m.p. 108° C decomposed |

The compounds of the invention are colorless, non-smelling crystalline materials which have a good solubility both in water and in organic solvents such as hydrocarbons, halogenated hydrocarbons, ethers, ketones, alcohols, carboxylic acids, esters, carboxylic acid amides and carboxylic acid nitriles.

ACTIVITY OF THE COMPOUNDS

The herbicidal action of the compounds of the invention appears from the following tests.

EXAMPLE 1

The indicated plants were treated in a hothouse in a preemergence application with the indicated compounds in an amount of 1 kg of active agent per about 2.5 acres. The agents were used in a uniform application to the ground in the form of an aqueous suspension of 500 liter per 2.5 acres. The results three weeks after the application showed that the compounds of the invention had a higher herbicidal activity and greater selectivity than the control compounds.

| Composition of the Invention | Peanut | Echinochloa c.g. | Sorghum h. | Setaria | Digitaria | Poa | Alopecurus | Avena f. | Galium |
| --- | --- | --- | --- | --- | --- | --- | --- | --- | --- |
| [5-(1,3,3-trimethylureido)-1,3,4-thiadiazol-2-ylsulfonyl]-acetic acid | 10 | 0 | 0 | 0 | 0 | 0 | 0 | 0 | 0 |
| [5-(1,3,3-trimethylureido)-1,3,4-thiadiazol-2-ylsulfonyl]-acetic acid, potassium salt | 10 | 0 | 0 | 0 | 0 | 0 | 0 | 0 | 0 |
| [5-(1,1,3-trimethylureido)-1,3,4-thiadiazol-2-ylsulfonyl]-acetic acid, ammonium salt | 8 | 1 | 0 | 0 | 0 | 0 | 0 | 0 | 0 |
| Control Compounds | | | | | | | | | |
| 1,1,3-trimethyl-3-(5-n-butyl-sulfonyl-1,3,4-thiadiazol-2-yl)-urea | 8 | 5 | 4 | 1 | 5 | 0 | 2 | 6 | 2 |

0 = total destruction
10 = unharmed

EXAMPLE 2

The listed plants were treated in a hothouse in a postemergence application with the indicated compounds in an amount of 1 kg of active agent per about 2.5 acres. The compounds were applied uniformly to the plants by spraying of an aqueous suspension of 500 liter per about 2.5 acres. In this case likewise it was found three weeks after application that the compounds of the invention had a better activity and higher selectivity than the control compounds.

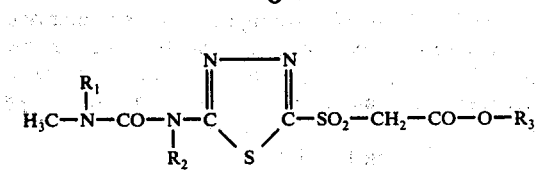

| Composition of the Invention | Pea-nut | Echino-chloa c.g. | Sorghum h. | Set-aria | Digi-taria | Poa | Alope-curus | Avena f. | Galium |
|---|---|---|---|---|---|---|---|---|---|
| [5-(1,3,3-trimethylureido)-1,3,4-thiadiazol-2-ylsulfonyl]-acetic acid | 10 | 0 | 0 | 0 | 0 | 0 | 0 | | |
| [5-(1,3,3-trimethylureido)-1,3,4-thiadiazol-2-ylsulfonyl]-acetic acid potassium salt | 10 | 0 | 0 | 0 | 0 | 0 | 0 | | |
| [5-(1,1,3-trimethylureido)-1,3,4-thiadiazol-2-ylsulfonyl]-acetic acid, ammonium salt | 8 | 0 | 0 | 0 | 0 | 2 | 1 | 0 | 0 |
| Control Compound 1,1,3-trimethyl-3-(5-n-butylsulfonyl-1,3,4-thiadiazol-2-yl)-urea | 5 | 2 | 3 | 0 | 4 | 0 | 2 | 0 | 0 |

0 = total destruction
10 = unharmed

In all of these tests the area of ground to which the compounds were applied was 1 hectar by the metric system which was roughly indicated as about 2.5 acres.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. (5-alkylureido-1,3,4-thiadiazol-2-ysulfonyl) acetic acid derivatives of the general formula in which $R_1$ and $R_2$ are hydrogen or methyl and $R_3$ is hydrogen alkyl of 1 to 4 carbon atoms, a univalent metal equivalent selected from the group consisting of Na, K, Ca/2, Mg/2 and $NH_4$, an ammonium group or an alkyl ammonium group selected from the group consisting of triethylammonium, tris-(2-hydroxy-(ethyl)-ammonium, tetramethylammonium and tetrabutylammonium.

2. The compound of claim 1 in which $R_1$ and $R_2$ are hydrogen or methyl, $R_3$ is hydrogen, alkyl of 1 to 4 carbon atoms, a univalent metal equivalent, an ammonium group or an alkyl ammonium group.

3. [5-(1,3,3-trimethylureido)-1,3,4-thiadiazol-2-ylsulfonyl]-acetic acid.

4. Potassium salt of [5-(1,3,3-trimethylureido)-1,3,4-thiadiazol-2-ylsulfonyl]-acetic acid.

5. Ammonium salt of [5-(1,3,3-trimethylureido)-1,3,4-thiadiazol-2-ylsulfonyl]-acetic acid.

* * * * *